United States Patent
Pasin et al.

(10) Patent No.: US 10,752,566 B2
(45) Date of Patent: Aug. 25, 2020

(54) SOLVENT COMPOSITIONS FOR USE AS REPLACEMENTS FOR SLOW EVAPORATING SOLVENTS

(71) Applicant: TBF ENVIRONMENTAL TECHNOLOGY INC., Surrey (CA)

(72) Inventors: David Anthony Pasin, Vancouver (CA); Shira Devorah Bogner, Vancouver (CA)

(73) Assignee: TBF ENVIRONMENTAL TECHNOLOGY INC., Surrey, B.C. (CA)

( * ) Notice: Subject to any disclaimer, the term of this patent is extended or adjusted under 35 U.S.C. 154(b) by 0 days.

(21) Appl. No.: 15/580,896

(22) PCT Filed: Jun. 2, 2016

(86) PCT No.: PCT/IB2016/053243
§ 371 (c)(1),
(2) Date: Dec. 8, 2017

(87) PCT Pub. No.: WO2016/198994
PCT Pub. Date: Dec. 15, 2016

(65) Prior Publication Data
US 2018/0362422 A1 Dec. 20, 2018

Related U.S. Application Data

(60) Provisional application No. 62/174,418, filed on Jun. 11, 2015.

(51) Int. Cl.
| | | |
|---|---|---|
| *C11D 7/50* | (2006.01) | |
| *C07C 25/13* | (2006.01) | |
| *B01F 1/00* | (2006.01) | |
| *C09D 9/00* | (2006.01) | |
| *C07D 317/36* | (2006.01) | |
| *C07F 7/08* | (2006.01) | |

(52) U.S. Cl.
CPC ............ *C07C 25/13* (2013.01); *B01F 1/00* (2013.01); *C07D 317/36* (2013.01); *C07F 7/0838* (2013.01); *C09D 9/005* (2013.01)

(58) Field of Classification Search
CPC .............. C11D 3/43; C11D 7/28; C11D 3/162
USPC ........................................................ 510/170
See application file for complete search history.

(56) References Cited

U.S. PATENT DOCUMENTS

| | | | |
|---|---|---|---|
| 6,929,702 B1 * | 8/2005 | Motsenbocker | C11D 3/43 134/40 |
| 2004/0157983 A1 * | 8/2004 | Halladay | C08J 7/126 524/588 |
| 2008/0280802 A1 * | 11/2008 | Dabela | B41N 3/00 510/170 |
| 2012/0010119 A1 | 1/2012 | Cunningham | |
| 2013/0017986 A1 * | 1/2013 | Dabela | B41N 3/00 510/170 |
| 2014/0065432 A1 * | 3/2014 | Wuerch | C09J 11/06 428/447 |
| 2018/0179129 A1 * | 6/2018 | Pasin | B01F 1/00 |

FOREIGN PATENT DOCUMENTS

| | | |
|---|---|---|
| CA | 2845415 A1 | 5/2014 |
| CA | 2988911 | 12/2017 |
| WO | PCT/IB2016/053243 | 6/2016 |

OTHER PUBLICATIONS

International Search Report and Written Opinion dated Aug. 18, 2016 by the International Searching Authority for Patent Application No. PCT/IB2016/053243, which was filed on Jun. 2, 2016 and published as WO 2016/198994 on Dec. 15, 2016 (Inventor—Pasin et al.; Applicant—TBF Environmental Technology, Inc.) (9 pages).
International Preliminary Report on Patentability dated Dec. 12, 2017 by the International Searching Authority for Patent Application No. PCT/IB2016/053243, which was filed on Jun. 2, 2016 and published as WO 2016/198994 on Dec. 15, 2016 (Inventor—Pasin et al.; Applicant—TBF Environmental Technology, Inc.) (6 pages).

* cited by examiner

*Primary Examiner* — Gregory E Webb
(74) *Attorney, Agent, or Firm* — Richard D. Okimaw

(57) ABSTRACT

The present disclosure provides, in part, a solvent composition for use as a replacement for slow evaporating solvents. The solvent composition may include para-Chlorobenzotrifluoride (PCBTF), a methylated organosilicon compound, and a carbonate ester.

19 Claims, No Drawings

SOLVENT COMPOSITIONS FOR USE AS REPLACEMENTS FOR SLOW EVAPORATING SOLVENTS

CROSS-REFERENCE TO RELATED PATENT APPLICATIONS

This application is a U.S. national phase application of International Application No. PCT/IB2016/053243 filed on Jun. 2, 2016, which claims benefit of U.S. Provisional Application No. 62/174,418, filed Jun. 11, 2015. The content of these earlier filed applications is hereby incorporated by reference in their entirety.

FIELD OF INVENTION

The present disclosure relates generally to solvent compositions. More specifically, the present disclosure relates to solvent compositions that may be used to replace slow evaporating solvents.

BACKGROUND OF THE INVENTION

Organic solvents, including slow evaporating solvents such as mineral spirits, Methyl Amyl Ketone (MAK), n-butyl acetate, cyclohexane, Aromatic 100 and Aromatic 150 and other hydrocarbons, and chlorinated or oxygenated solvents are used in a number of applications. Many of these solvents have toxic and/or environmentally deleterious properties. For example, human and animal studies indicate that exposure to these chemicals can have detrimental effects on the central nervous system as well as be potentially carcinogenic.

Furthermore, almost all organic solvents are highly volatile and, of the total quantity released to the environment, a significant percentage eventually enters the troposphere. As such, these solvents have been designated volatile organic compounds (or "VOCs") and are regulated. A number of compounds or solvents have been classified as VOC-exempt in the United States (U.S.) by the Environmental Protection Agency (EPA), and/or the South Coast Air Quality Management District (SCAQMD) of California and in Canada by the National Pollutant Release Inventory (NPRI).

Mineral spirits, also known as mineral turpentine, turpentine substitute, petroleum spirits, solvent naphtha (petroleum), Varsol, Stoddard solvent or, generically, "paint thinner", are petroleum-derived and are a mixture of aliphatic and alicyclic C7 to C12 liquid hydrocarbons with a clear, transparent appearance. Mineral spirits are used as a common organic solvent in painting and decorating, as an extraction solvent, as a degreasing solvent, as a solvent in aerosols, paints, coatings, stains, wood preservatives, lacquers, varnishes, and asphalt products, and as s surface cleaner, parts cleaner and a general industrial cleaner and degreaser. Mineral spirits are a VOC emitter.

SUMMARY OF THE INVENTION

The present disclosure provides, in part, a solvent composition including para-chlorobenzotrifluoride (PCBTF), a methylated organosilicon compounds, and a carbonate ester.

In one aspect, the present disclosure provides a solvent composition including para-Chlorobenzotrifluoride (PCBTF) in an amount of about 50% to about 65% by volume of the solvent composition; a methylated organosilicon compound in an amount of about 23% to about 50% by volume of the solvent composition; and a carbonate ester in an amount of about 0% to about 12% by volume of the solvent composition.

In some embodiments, the para-Chlorobenzotrifluoride (PCBTF) may include about 60% to about 65% by volume of the solvent composition; the first methylated organosilicon compound may include about 25% to about 30% by volume of the solvent composition; and the carbonate ester may include about 10% to about 12% by volume of the solvent composition.

In some embodiments, the para-chlorobenzotrifluoride (PCBTF) may include about 60% by volume of the solvent composition; the methylated organosilicon compound may be decamethyltetrasiloxane (DMTS), and may include about 28% by volume of the solvent composition; and the carbonate ester may be propylene carbonate (PC) and may include about 12% by volume of the solvent composition.

In some embodiments, the para-chlorobenzotrifluoride (PCBTF) may include about 63% by volume of the solvent composition; the methylated organosilicon compound may be decamethyltetrasiloxane (DMTS), and may include about 27% by volume of the solvent composition; and the carbonate ester may be propylene carbonate (PC) and may include about 10% by volume of the solvent composition.

In some embodiments, the para-chlorobenzotrifluoride (PCBTF) may include about 65% by volume of the solvent composition; the methylated organosilicon compound may be decamethyltetrasiloxane (DMTS), and may include about 25% by volume of the solvent composition; and the carbonate ester may be propylene carbonate (PC) and may include about 10% by volume of the solvent composition.

In some embodiments, the solvent composition may have a calculated flash point of at least 50° C.

In some embodiments, the solvent composition may have a calculated evaporation rate of at most 0.7.

In some aspects, the present disclosure provides a kit or commercial package comprising a solvent composition, as described herein, together with instructions for use.

In some embodiments, the present disclosure provides a solvent composition, as described herein, for use as a replacement for slow evaporating solvents.

In some embodiments, the present disclosure provides a solvent composition, as described herein, for use as a replacement for mineral spirits, methyl amyl ketone (mak), cyclohexane, n-butyl acetate, Aromatic 100 or Aromatic 150.

In some embodiments, the present disclosure provides a solvent composition, as described herein, for use as a solvent.

In some embodiments, the present disclosure provides a solvent composition, as described herein, for use as a primary or co-solvent for paints, varnishes, coatings, inks, or adhesives, thin films.

In some embodiments, the present disclosure provides a solvent composition, as described herein, for use in the manufacturing and/or formulation of paints, varnishes, coatings, wood preservatives, lacquers, shoe polish, thin films or varnishes.

In some embodiments, the present disclosure provides a solvent composition, as described herein, for use as a paint thinner, paint remover, cleaner, degreaser, and/or adhesive remover.

Other aspects and features of the present disclosure will become apparent to those ordinarily skilled in the art upon review of the following description of specific examples.

DETAILED DESCRIPTION

The present disclosure provides, in part, a solvent composition including para-chlorobenzotrifluoride (PCBTF), a methylated organosilicon compound, and optionally a carbonate ester.

para-Chlorobenzotrifluoride (PCBTF) has the formula $C_7H_4ClF_3$. It is an industrial solvent which is heavy (specific gravity of 1.34) with a pungent odour. PCBTF is VOC-exempt. In some embodiments, PCBTF may be present in the solvent composition in any amount between about 50% v/v to about 65% v/v, or between about 55% v/v to about 65% v/v, or between about 50% v/v to about 60% v/v, or between about 50% v/v to about 65% v/v, or between about 55% v/v to about 60% v/v, or between about 60% v/v to about 65% v/v, or between about 50% v/v to about 55% v/v, or any value in between or inclusive of the indicated ranges, for example, about 50% v/v, 51% v/v, 52% v/v, 53% v/v, 54% v/v, 55% v/v, 56% v/v, 57% v/v, 58% v/v, 59% v/v, 60% v/v, 61% v/v, 62% v/v, 63% v/v, 64% v/v, 65% v/v, etc.

By "methylated organosilicon compound," as used herein, is meant an organic compound with two or more siloxane functional groups saturated with methyl groups. The methylated organosilicon compound may be VOC-exempt.

In some embodiments, the methylated organosilicon compound may be present in the solvent composition in any amount between about 23% v/v to about 50% v/v, or between about 23% v/v to about 30% v/v, or between about 30% v/v to about 50% v/v, or between about 25% v/v to about 35% v/v, or any value in between or inclusive of the indicated ranges, for example, about 23% v/v, 24% v/v, 25% v/v, 26% v/v, 27% v/v, 28% v/v, 29% v/v, 30% v/v, 31% v/v, 32% v/v, 33% v/v, 34% v/v, 35% v/v, 36% v/v, 37% v/v, 38% v/v, 39% v/v, 40% v/v, 41% v/v, 42% v/v, 43% v/v, 44% v/v, 45% v/v, 46% v/v, 47% v/v, 48% v/v, 49% v/v, 50% v/v, etc.

Hexamethyldisiloxane (HMDS) has the formula $C_6H_{18}OSi_2$. It is a colourless liquid and has a slight odour. HMDS is VOC-exempt. In some embodiments, the methylated organosilicon compound may be HMDS, which may be present in the solvent composition in any amount between about 23% v/v to about 50% v/v, or between about 23% v/v to about 30% v/v, or between about 30% v/v to about 50% v/v, or between about 25% v/v to about 35% v/v, or any value in between or inclusive of the indicated ranges, for example, about 23% v/v, 24% v/v, 25% v/v, 26% v/v, 27% v/v, 28% v/v, 29% v/v, 30% v/v, 31% v/v, 32% v/v, 33% v/v, 34% v/v, 35% v/v, 36% v/v, 37% v/v, 38% v/v, 39% v/v, 40% v/v, 41% v/v, 42% v/v, 43% v/v, 44% v/v, 45% v/v, 46% v/v, 47% v/v, 48% v/v, 49% v/v, 50% v/v, etc.

Octamethyltrisiloxane (OMTS) has the formula $C_8H_{24}O_2Si_3$. It is a colourless liquid and has a slight odour. OMTS is VOC-exempt. In some embodiments, the methylated organosilicon compound may be OMTS, which may be present in the solvent composition in any amount between about 23% v/v to about 50% v/v, or between about 23% v/v to about 30% v/v, or between about 30% v/v to about 50% v/v, or between about 25% v/v to about 35% v/v, or any value in between or inclusive of the indicated ranges, for example, about 23% v/v, 24% v/v, 25% v/v, 26% v/v, 27% v/v, 28% v/v, 29% v/v, 30% v/v, 31% v/v, 32% v/v, 33% v/v, 34% v/v, 35% v/v, 36% v/v, 37% v/v, 38% v/v, 39% v/v, 40% v/v, 41% v/v, 42% v/v, 43% v/v, 44% v/v, 45% v/v, 46% v/v, 47% v/v, 48% v/v, 49% v/v, 50% v/v, etc.

Decamethyltetrasiloxane (DMTS) has the formula $C_{10}H_{30}O_3Si_4$. It is a colourless liquid and has a slight odour. DMTS is VOC-exempt. In some embodiments, the methylated organosilicon compound may be HMDS, which may be present in the solvent composition in any amount between about 23% v/v to about 50% v/v, or between about 23% v/v to about 30% v/v, or between about 30% v/v to about 50% v/v, or between about 25% v/v to about 35% v/v, or any value in between or inclusive of the indicated ranges, for example, about 23% v/v, 24% v/v, 25% v/v, 26% v/v, 27% v/v, 28% v/v, 29% v/v, 30% v/v, 31% v/v, 32% v/v, 33% v/v, 34% v/v, 35% v/v, 36% v/v, 37% v/v, 38% v/v, 39% v/v, 40% v/v, 41% v/v, 42% v/v, 43% v/v, 44% v/v, 45% v/v, 46% v/v, 47% v/v, 48% v/v, 49% v/v, 50% v/v, etc.

By "carbonate ester," as used herein, is meant a carbonic acid alkyl ($C_1$—$C_4$) ester having the formula $R^1OCOOR^2$, where $OR^1$ and $OR^2$ are each independently $C_1$—$C_4$ alkoxy groups. "Alkoxy" refers to an oxygen atom bound to a straight or branched hydrocarbon chain group consisting solely of carbon and hydrogen atoms, containing no unsaturation and including, for example, from one to four carbon atoms, such as 1, 2, 3, or 4 carbon atoms. $R^1$ and $R^2$ may be identical, different, or connected via the alkyl portion to form a ring.

In some embodiments, the carbonate ester may be present in the solvent composition in any amount between about 0% v/v to about 12% v/v, or about 5% v/v to about 12% v/v, or about 0% v/v to about 5% v/v, or about 8% v/v to about 12% v/v, or any value in between or inclusive of the indicated ranges, for example, about 0% v/v, 1% v/v, 2% v/v, 3% v/v, 4% v/v, 5% v/v, 6% v/v, 7% v/v, 8% v/v, 9% v/v, 10% v/v, 11 v/v, 12% v/v, etc.

Propylene carbonate (PC) has the formula $C_4H_6O_3$. It is a polar, aprotic compound. PC is VOC-exempt. In some embodiments, the carbonate ester may be PC, which may be present in the solvent composition in any amount between about 0% v/v to about 12% v/v, or about 5% v/v to about 12% v/v, or about 0% v/v to about 5% v/v, or about 8% v/v to about 12% v/v, or any value in between or inclusive of the indicated ranges, for example, about 0% v/v, 1% v/v, 2% v/v, 3% v/v, 4% v/v, 5% v/v, 6% v/v, 7% v/v, 8% v/v, 9% v/v, 10% v/v, 11 v/v, 12% v/v, etc.

In some embodiments, the disclosure may provide a solvent composition including PCBTF in an amount between about 50% v/v and about 65% v/v, a methylated organosilicon compound in an amount between about 23% and about 50%, and a carbonate ester in an amount between about 0% v/v and about 12% v/v.

In some embodiments, the solvent composition may include PCBTF in an amount between about 50% v/v and about 65% v/v, DMTS in an amount between about 23% and about 50%, and a carbonate ester in an amount between about 0% v/v and about 12% v/v.

In some embodiments, the solvent composition may include PCBTF in an amount between about 50% v/v and about 65% v/v, a methylated organosilicon compound in an amount between about 23% and about 50%, and PC in an amount between about 0% v/v and about 12% v/v.

In some embodiments, the solvent composition may include PCBTF in an amount between about 50% v/v and about 65% v/v, DMTS in an amount between about 23% and about 50%, and PC in an amount between about 0% v/v and about 12% v/v.

In some embodiments, the solvent composition may include PCBTF in an amount of about 60% v/v (about 70.7 wt %), DMTS in an amount of about 30% v/v (about 19.2 wt %), and PC in an amount of about 10% v/v (about 10.1 wt %).

In some embodiments, the solvent composition may include PCBTF in an amount of about 63% v/v (about 70.7 wt %), DMTS in an amount of about 27% v/v (about 19.2 wt %), and PC in an amount of about 10% v/v (about 10.1 wt %).

In some embodiments, the solvent composition may include PCBTF in an amount of about 65% v/v (about 72.3 wt %), DMTS in an amount of about 25% v/v (about 17.6 wt %), and PC in an amount of about 10% v/v (about 10.1 wt %).

By "about" is meant a variance (plus or minus) from a value or range of 5% or less, for example, 0.5%, 1%, 1.5%, 2.0%, 2.5%, 3.0%, 3.5%, 4.0%, 4.5%, 5.0%, etc.

It is to be understood that varying the concentration of a reagent in a composition will generally require a corresponding adjustment (increase or decrease) in the amount of the other reagents in a composition according to the present disclosure.

In some embodiments, while not bound to any particular theory, HMDS, OMTS and/or DMTS may be used as ingredients that do not contribute any hydrogen bonding capability or polarity of a composition according to the present disclosure.

In some embodiments, while not bound to any particular theory, HMDS, OMTS and/or DMTS may be used to increase the calculated or measured solvency of a composition according to the present disclosure.

In some embodiments, while not bound to any particular theory, OMTS and/or DMTS may also to decrease the calculated or measured evaporation rate of a composition according to the present disclosure.

In some embodiments, while not bound to any particular theory, OMTS and/or DMTS may be used to increase the flashpoint of a composition according to the present disclosure.

In some embodiments, while not bound to any particular theory, PC may be used to decrease the calculated or measured evaporation rate of a composition according to the present disclosure.

In some embodiments, while not bound to any particular theory, PC may be used to increase the flashpoint of a composition according to the present disclosure.

In some embodiments, while not bound to any particular theory, PCBTF may be used to increase the calculated or measured solvency of a composition according to the present disclosure.

In some embodiments, a solvent composition according to the present disclosure may include reagents that are not classified as hazardous air pollutants (HAPs), as environmentally hazardous, or as ozone-depleting, or as VOCs.

In some embodiments, a solvent composition according to the present disclosure may include compounds or reagents that are VOC-exempt. Such compositions are useful in reducing VOC emissions. MA, PC, HMDS, OMTS, DMTS and PCBTF are presently VOC-exempt.

A compound's maximum incremental reactivity (MIR) value is a measure of the compound's ability to generate ground-level ozone due to photochemical degradation. The lower the MIR value, the less ozone (and, accordingly, the less smog) that is generated by the compound. In some embodiments, a solvent composition according to the present disclosure may have a MIR value lower than mineral spirits (MIR 0.82-2.47). In alternative embodiments, compositions according to the present disclosure may have a MIR value of 0.097.

Compositions having a high flash point are useful due to safety reasons, for example, during transport or manufacture or for consumer use. In some embodiments, a solvent composition according to the present disclosure may have a higher flash point than mineral spirits (about 40° C.). In some embodiments, a solvent composition according to the present disclosure may have a calculated flash point of at least about 40.0° C., for example, at least about 40.0° C., 41.0° C., 42.0° C., 43.0° C., 44.0° C., 45.0° C., 46.0° C., 47.0° C., 48.0° C., 49.0° C., 50.0° C., 51.0° C., 52.0° C., 53.0° C., 54.0° C., 55.0° C., 56.0° C., 57.0° C., 58.0° C., 59.0° C., 60.0° C., 61.0° C., 62.0° C., 63.0° C., 64.0° C., 65.0° C., 70.0° C., 75.0° C., 80.0° C., 85.0° C., 90.0° C., 95.0° C., or more. In some embodiments, a solvent composition according to the present disclosure may have an experimentally-determined flash point of at least about 20.0° C., for example, at least about 20.0° C., 25.0° C., 30.0° C., 35.0° C., 40.0° C., 41.0° C., 42.0° C., 43.0° C., 44.0° C., 45.0° C., 46.0° C., 47.0° C., 48.0° C., 49.0° C., 50.0° C., 51.0° C., 52.0° C., 53.0° C., 54.0° C., 55.0° C., 56.0° C., 57.0° C., 58.0° C., 59.0° C., 60.0° C., 61.0° C., 62.0° C., 63.0° C., 64.0° C., 65.0° C., 70.0° C., 75.0° C., 80.0° C., 85.0° C., 90.0° C., 95.0° C., or more. In some embodiments, a solvent composition according to the present disclosure may have a flash point of between about 20.0° C. to about 95.0° C., or any value in between. In alternative embodiments, a solvent composition according to the present disclosure may have a flash point of about 43.5° C.

In some embodiments, a solvent composition according to the present disclosure may have low toxicity as determined, for example by one or more of oral $LD_{50}$ on rats, biodegradability, teratogenicity, carcinogenicity and/or hepatic and renal toxicity measurements, which can be determined using standard methods. In some embodiments, a solvent composition according to the present disclosure may contain reagents classified as non-carcinogenic. A solvent composition according to the present disclosure may have an $LD_{50}$ of 5000 mg/kg or more.

Evaporation rates can be expressed relative to the evaporation of n-butyl acetate (=1), as a standard. Evaporation rates may be calculated or experimentally-determined. In some embodiments, a solvent composition according to the present disclosure may have a calculated evaporation rate that is about 6 times faster, at ambient or room temperatures, than that of mineral spirits which has an evaporation rate of 0.1 (n-Butyl Acetate=1). In some embodiments, a solvent composition according to the present disclosure may have a calculated evaporation rate of about 0.61 at ambient or room temperatures. In some embodiments, a solvent composition according to the present disclosure may have an evaporation rate of about 0.1. In some embodiments, a solvent composition according to the present disclosure may have an evaporation rate of about 0.05 to about 1.5, or between about 0.5 to about 0.7, or any value in between or inclusive of these ranges, such as about 0.05, 0.1, 0.2, 0.3, 0.4, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.8, 0.9, 1.0, 1.1, 1.2, 1.3, 1.4, 1.5, etc. at ambient or room temperatures. In some embodiments, a solvent composition according to the present disclosure may have a calculated evaporation rate of about between 0.05 to about 1.5, or between about 0.5 to about 0.7, or any value in between or inclusive of these ranges, such as about 0.05, 0.1, 0.2, 0.3, 0.4, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.8, 0.9, 1.0, 1.1, 1.2, 1.3, 1.4, 1.5, etc. at ambient or room temperatures. In some embodiments, a solvent composition according to the present disclosure may have an experimentally-determined evaporation rate between about 0.05 to about 1.5, or between about 0.5 to about 0.7, or any value in between or inclusive of these ranges such as about 0.05, 0.1, 0.2, 0.3, 0.4, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.8, 0.9, 1.0, 1.1, 1.2, 1.3, 1.4, 1.5, etc. at ambient or room temperatures.

In some embodiments, a solvent composition according to the present disclosure may be substantially anhydrous, for example, containing less than 0.05 wt % water. In alternative embodiments, a solvent composition according to the present disclosure may contain less than 500 ppm of water.

In some embodiments, a solvent composition according to the present disclosure may be substantially immiscible with water.

In some embodiments, a solvent composition according to the present disclosure may have a purity of, for example, at least 99.5%, for example, at least 99.6%, 99.7%, 99.8%, 99.9%, or 100%. In alternative embodiments, PCBTF may have a purity of, for example, at least 99.5%. In alternative embodiments, DMTS may have a purity of, for example, at least 99.5%. In alternative embodiments, PC may have a purity of, for example, at least 99.5%.

In some embodiments, a solvent composition according to the present disclosure may have a viscosity of about 1.18 cP. In some embodiments, a solvent composition according to the present disclosure may have a viscosity similar to mineral spirits, which is about 0.74-1.65 cps.

In some embodiments, a solvent composition according to the present disclosure may have improved solvency, a Kauri Butanol (Kb) value of about 54.47, relative to, for example mineral spirits, which has a Kb value of about 29 to about 36. This may, in some embodiments, permit the use of less of a solvent composition according to the present disclosure, when compared to compositions containing mineral spirits.

In some embodiments, a solvent composition according to the present disclosure may have a specific gravity of about 1.19 g/ml.

In some embodiments, a solvent composition according to the present disclosure may have performance characteristics approximating that of mineral spirits, as described herein or known in the art.

In some embodiments, a solvent composition according to the present disclosure may be recycled through distillation at an appropriate temperature (for example, above the initial boiling point of approximately 147.5° C. (297.5° F.).

In some embodiments, a solvent composition according to the present disclosure may have a mild odor. In some embodiments, solvent compositions according to the present disclosure may include reagents that do not have an unpleasant and/or strong odor.

In some embodiments, the present disclosure provides a solvent composition consisting essentially of para-chlorobenzotrifluoride (PCBTF), a methylated organosilicon compound, and (optionally) a carbonate ester, as described herein. By "consisting essentially of" is meant that inert and/or neutral compounds may be present in the solvent composition without affecting its physical properties, such as flash point or evaporation rate. Accordingly, compounds that may reduce the flash point of the solvent composition below 20° C., or increase the evaporation rate over 1.5, are specifically excluded. In some embodiments, halogenating agents or certain halogen-bearing compounds, including hypohalous, activated halo substituted compounds, and halogen donors (such as tertiary butyl hypochlorite, tertiary butyl hypobromite, diethylbromomalonate, α-bromoacetophenone, bromoacetic acid, cinnamyl bromide, 1,4-dibromo-2-butene, iodoacetic acid, bromodiphenylmethane, 9-bromofluorene, diethyl bromomalonate, benzoyl bromide, cinnamyl bromide, 1,4-dibromo-2-butene, bromoacetic acid, 1,4-dibromo-2,3-butanedione, diethyl dibromomalonate, N-monohaloalkylurethane, N,N-dihaloalkylurethane, N,N-dichloroethylurethane, N,N-dibromoethylurethane, N,N-dichloropropylurethane, N,N-dibromopropylurethane, N,N-dichlorodibenzylurethane, N,N-dibromobenzylurethane dibromoacetonitrile, tribromoacetaldehyde, alpha-bromoisobutyrophenone, ethyl 2-bromoisobutyrate, α,α,α,α-tetrabromo-α-xylene, 9,10-dibromoanthracene,N-chloroparatoluenesulphonamide, N,N-dihalogenarylsulfonamides such as N,N-dichloro-p-toluenesulfonamide, N,N-dibromotoluenesulfonamide, N,N-dichlorobenzenesulfonamide, N,N-dibromobenzenesulfonamide, halomethyl ether, thiocyanogen, iodine azide, bromine azide, iodine chloride, iodine bromide, trichloroacetic acid iodide, acetic acid bromide, iodine nitrate, alkyl hypohalite, alkyl thionylchloride, aryl thionylchloride, nitrosyl chloride, nitrosyl bromide, etc. are specifically excluded. In some embodiments, cyclohexanes are specifically excluded.

In some embodiments, a solvent composition according to the present disclosure may be useful in replacing slow evaporating solvents. By "slow evaporating solvents" is meant a solvent that has an evaporation rate of about 1.5 or less (where n-BuAc=1). In some embodiments, a solvent composition according to the present disclosure may be useful in replacing one or more of mineral spirits, methyl amyl ketone (mak), cyclohexane, n-butyl acetate, Aromatic 100 or Aromatic 150 in aliphatic, aromatic and ketone paint and coatings resin systems. The solvent compositions can be used, for example, as a solvent in various applications. Examples of contemplated applications include, without limitation: use as paint thinner; use as a paint remover; use as a cleaner; and use as a cleaner/degreaser.

In some embodiments, a solvent composition according to the present disclosure may be useful in the manufacturing and formulation of paints, coatings, wood preservatives, lacquers, varnishes, as well as in industrial, commercial cleaning/de-greasing applications.

In some embodiments, a solvent composition according to the present disclosure may be useful in paints and coating formulations and/or cleaning, paint removers.

In some embodiments, a solvent composition according to the present disclosure may be useful as a surface preparation, general purpose surface wipe cleaner (for example, prior to painting), general and/or heavy duty degreaser, brake cleaner, etc.

In some embodiments, a solvent composition as described herein may be used in the formulation of automotive care and service products such as cleaners, degreasers, upholstery care, tire care, or brake cleaners.

In some embodiments a solvent composition as described herein may be used as a co-solvent in the formulation of paints, coatings, inks, adhesives or foam, and/or as a primary or co-solvent in the formulation of hard surface cleaners, for surface preparation, and/or general and heavy duty degreasing.

It is to be understood that a solvent composition according to the present disclosure can be used in a variety of applications in which mineral spirits are traditionally used, and can be used to replace mineral spirits in such applications. Accordingly, it is to be understood that the ultimate amounts of a solvent composition according to the present disclosure may vary depending on the ultimate use and final composition of the product in which the solvent composition according to the present disclosure is being used.

EXAMPLES

Candidate compounds were selected using a number of environmental criteria, such as low flammability, safety, VOC exempt status, and sustainable sourcing.

Candidate compounds were also selected based on their physicochemical properties as, for example, determined from manufacturers' Material Safety Data Sheets, various chemical databases, such as CHEMnetBASE or Chemspider. Candidates with relatively high flash points, low toxicity and low vapor pressures, when compared with mineral spirits, etc. were selected for further testing.

Example 1

A solvent composition (Formulation 1) was prepared by mixing the following:
 5% (v/v) or 5.2 (wt %) PC (CAS 108-32-7)
 35% (v/v) or 25.6 (wt %) DMTS (CAS 141-62-8)
 60% (v/v) or 69.2 (wt %) PCBTF (CAS 98-56-6)

Formulation 1 has a MIR value of 0.080, a predicted flash point of about 52.6° C., and a calculated evaporation rate=0.59.

Example 2

A solvent composition (Formulation 2) was prepared by mixing the following:
 5% (v/v) or 5.0 (wt %) PC (CAS 108-32-7)
 30% (v/v) or 21.5 (wt %) DMTS (CAS 141-62-8)
 65% (v/v) or 73.4 (wt %) PCBTF (CAS 98-56-6)

Formulation 2 has a MIR value of 0.086, a predicted flash point of about 51.9° C., and a calculated evaporation rate=0.63.

Example 3

A solvent composition (Formulation 3) was prepared by mixing the following:
 7.5% (v/v) or 7.7 (wt %) PC (CAS 108-32-7)
 30% (v/v) or 21.6 (wt %) DMTS (CAS 141-62-8)
 62.5% (v/v) or 70.8 (wt %) PCBTF (CAS 98-56-6)

Formulation 3 has a MIR value of 0.90, a predicted flash point of about 54.2° C., and a calculated evaporation rate=0.61.

Example 4

A solvent composition (Formulation 4) was prepared by mixing the following:
 10% (v/v) or 10.3 (wt %) PC (CAS 108-32-7)
 30% (v/v) or 21.6 (wt %) DMTS (CAS 141-62-8)
 60% (v/v) or 68.1 (wt %) PCBTF (CAS 98-56-6)

Formulation 4 has a MIR value of 0.094, a predicted flash point of about 56.5° C., and a calculated evaporation rate=0.59.

Example 5

A solvent composition (Formulation 5) was prepared by mixing the following:
 10% (v/v) or 10.0 (wt %) PC (CAS 108-32-7)
 25% (v/v) or 17.6 (wt %) DMTS (CAS 141-62-8)
 65% (v/v) or 72.3 (wt %) PCBTF (CAS 98-56-6)

Formulation 5 has a MIR value of 0.10, a predicted flash point of about 55.8° C., and a calculated evaporation rate=0.62.

Example 6

A solvent composition (Formulation 6) was prepared by mixing the following:
 10% (v/v) or 10.5 (wt %) PC (CAS 108-32-7)
 35% (v/v) or 25.8 (wt %) DMTS (CAS 141-62-8)
 55% (v/v) or 63.8 (wt %) PCBTF (CAS 98-56-6)

Formulation 6 has a MIR value of 0.089, a predicted flash point of about 57.2° C., and a calculated evaporation rate=0.55.

Example 7

A solvent composition (Formulation 7) was prepared by mixing the following:
 10% (v/v) or 10.1 (wt %) PC (CAS 108-32-7)
 27% (v/v) or 19.2 (wt %) DMTS (CAS 141-62-8)
 63% (v/v) or 70.7 (wt %) PCBTF (CAS 98-56-6)

Formulation 7 has a MIR value of 0.097, a predicted flash point of about 56.0° C., a calculated evaporation rate=0.61, and an experimentally-determined evaporation rate of 0.1.

The physical/chemical characteristics of Formulation 7 based on weighted averages (% vol) of the individual components (with the exception of boiling point, evaporation rate, Kauri Butanol value and flash point (tag closed cup), which were determined experimentally), were as follows:

Physical/Chemical Characteristics

| | |
|---|---|
| Upper Explosive Limit (UEL %) | 8.72 |
| Lower Explosive Limit (LEL %) | 1.28 |
| Auto Ignition Temp (° C.) | 452.5 (846.5° F.) |
| Molecular Weight (g/mol) | — |
| Flashpoint (° C.) | 43.5 (110.3° F.) |
| Initial Boiling Point (° C.) | 147.5 (297.5° F.) |
| Melting Point (° C.) | −44.1 (−47.4° F.) |
| Density (g/mL @ 25° C.) | 1.19 |
| Viscosity (cP @ 25° C.) | 1.18 |
| Surface Tension (dynes/cm) | 24.53 |
| Specific Gravity | 1.19 |
| Solubility in $H_2O$ (g/mL) | 0.026 |
| Evaporation Rate (n-Butyl Acetate = 1) | 0.1 |
| Vapour Pressure (mm Hg @ 20° C.) | 3.46 |
| Vapour Density (mm Hg Air = 1) | 4.53 |
| Kauri Butanol ($K_b$) Value | 54.47 |
| Maximum Incremental Reactivity (MIR) | 0.097 |
| Purity (Wt % Min) | — |
| Water Content (ppm) | — |
| Colour (Alpha, max) | — |
| Volatility (%) | — |
| Hansen solubility parameters (MPA) | 17.2 |
| δD (dispersion) | 13.9 |
| δP (polar) | 8.3 |
| δH (hydrogen bonding) | 3.4 |

Example 8

A solvent composition (Formulation 8) was prepared by mixing the following:
 11% (v/v) or 11.2 (wt %) PC (CAS 108-32-7)
 29% (v/v) or 20.8 (wt %) DMTS (CAS 141-62-8)
 60% (v/v) or 67.9 (wt %) PCBTF (CAS 98-56-6)

Formulation 8 has a MIR value of 0.097, a predicted flash point of about 57.2° C., and a calculated evaporation rate=0.58.

Example 9

A solvent composition (Formulation 9) was prepared by mixing the following:
- 12% (v/v) or 12.2 (wt %) PC (CAS 108-32-7)
- 28% (v/v) or 20.0 (wt %) DMTS (CAS 141-62-8)
- 60% (v/v) or 67.7 (wt %) PCBTF (CAS 98-56-6)

Formulation 9 has a MIR value of 0.10, a predicted flash point of about 58.0° C., and a calculated evaporation rate=0.58.

Example 10

A solvent composition (Formulation 10) was prepared by mixing the following:
- 13% (v/v) or 13.2 (wt %) PC (CAS 108-32-7)
- 27% (v/v) or 19.3 (wt %) DMTS (CAS 141-62-8)
- 60% (v/v) or 67.5 (wt %) PCBTF (CAS 98-56-6)

Formulation 10 has a MIR value of 0.10, a predicted flash point of about 58.8° C., and a calculated evaporation rate=0.58.

Example 11

A solvent composition (Formulation 11) was prepared by mixing the following:
- 14% (v/v) or 14.2 (wt %) PC (CAS 108-32-7)
- 26% (v/v) or 18.5 (wt %) DMTS (CAS 141-62-8)
- 60% (v/v) or 67.3 (wt %) PCBTF (CAS 98-56-6)

Formulation 11 has a MIR value of 0.11, a predicted flash point of about 59.6° C., and a calculated evaporation rate=0.58.

Example 12

A solvent composition (Formulation 12) was prepared by mixing the following:
- 15% (v/v) or 15.2 (wt %) PC (CAS 108-32-7)
- 25% (v/v) or 17.7 (wt %) DMTS (CAS 141-62-8)
- 60% (v/v) or 67.1 (wt %) PCBTF (CAS 98-56-6)

Formulation 12 has a MIR value of 0.11, a predicted flash point of about 60.4° C., and a calculated evaporation rate=0.58.

Example 13

A solvent composition (Formulation 13) was prepared by mixing the following:
- 20% (v/v) or 19.9 (wt %) PC (CAS 108-32-7)
- 20% (v/v) or 14.0 (wt %) DMTS (CAS 141-62-8)
- 60% (v/v) or 66.1 (wt %) PCBTF (CAS 98-56-6)

Formulation 13 has a MIR value of 0.12, a predicted flash point of about 64.2° C., and a calculated evaporation rate=0.57.

Example 14

A solvent composition (Formulation 14) was prepared by mixing the following:
- 25% (v/v) or 24.5 (wt %) PC (CAS 108-32-7)
- 15% (v/v) or 10.3 (wt %) DMTS (CAS 141-62-8)
- 60% (v/v) or 65.2 (wt %) PCBTF (CAS 98-56-6)

Formulation 14 has a MIR value of 0.14, a predicted flash point of about 68.1° C., and a calculated evaporation rate=0.56.

Example 15

A solvent composition (Formulation 15) was prepared by mixing the following:
- 10% (v/v) or 10.6 (wt %) PC (CAS 108-32-7)
- 38% (v/v) or 28.3 (wt %) DMTS (CAS 141-62-8)
- 52% (v/v) or 61.1 (wt %) PCBTF (CAS 98-56-6)

Formulation 15 has a MIR value of 0.0.085, a predicted flash point of about 57.6° C., and a calculated evaporation rate=0.53.

Example 16

A solvent composition (Formulation 16) was prepared by mixing the following:
- 10% (v/v) or 10.7 (wt %) PC (CAS 108-32-7)
- 39% (v/v) or 29.2 (wt %) DMTS (CAS 141-62-8)
- 51% (v/v) or 60.2 (wt %) PCBTF (CAS 98-56-6)

Formulation 16 has a MIR value of 0.084, a predicted flash point of about 57.7° C., and a calculated evaporation rate=0.61.

Example 17

A solvent composition (Formulation 17) was prepared by mixing the following:
- 10% (v/v) or 10.7 (wt %) PC (CAS 108-32-7)
- 40% (v/v) or 30.0 (wt %) DMTS (CAS 141-62-8)
- 50% (v/v) or 59.2 (wt %) PCBTF (CAS 98-56-6)

Formulation 17 has a MIR value of 0.83, a predicted flash point of about 57.9° C., and a calculated evaporation rate=0.51.

Example 18

A solvent composition (Formulation 18) was prepared by mixing the following:
- 10% (v/v) or 10.8 (wt %) PC (CAS 108-32-7)
- 41% (v/v) or 31.0 (wt %) DMTS (CAS 141-62-8)
- 49% (v/v) or 58.3 (wt %) PCBTF (CAS 98-56-6)

Formulation 18 has a MIR value of 0.82, a predicted flash point of about 58.0° C., and a calculated evaporation rate=0.50.

Example 19

A solvent composition (Formulation 19) was prepared by mixing the following:
- 10% (v/v) or 10.8 (wt %) PC (CAS 108-32-7)
- 42% (v/v) or 31.8 (wt %) DMTS (CAS 141-62-8)
- 48% (v/v) or 57.4 (wt %) PCBTF (CAS 98-56-6)

Formulation 19 has a MIR value of 0.081, a predicted flash point of about 58.2° C., and a calculated evaporation rate=0.50.

Example 20

A solvent composition (Formulation 20) was prepared by mixing the following:
- 50% (v/v) or 38.8 (wt %) DMTS (CAS 141-62-8)
- 50% (v/v) or 61.2 (wt %) PCBTF (CAS 98-56-6)

Formulation 20 has a MIR value of 0.055, a predicted flash point of about 50.1° C., and a calculated evaporation rate=0.53.

Example 21

A solvent composition (Formulation 21) was prepared by mixing the following:
12% (v/v) or 12.0 (wt %) PC (CAS 108-32-7)
23% (v/v) or 16.1 (wt %) DMTS (CAS 141-62-8)
65% (v/v) or 71.9 (wt %) PCBTF (CAS 98-56-6)

Formulation 21 has a MIR value of 0.105, a predicted flash point of about 57.3° C., and a calculated evaporation rate=0.62.

Example 22

A solvent composition (Formulation 22) was as follows:
100% (v/v) or 100% Mineral Spirits from Recochem Inc. (CAS 64742-88-7)

Formulation 22 has a reported MIR value of 0.82-2.47, a reported flash point of about 42° C., and a reported evaporation rate=0.1.

Example 23

Several compounds were combined in different initial blends (Table 1). Blends were formulated with predicted flash points>45° C. (113° F.) and calculated evaporation rates within the range of 0.5-0.65 (vs. n-Butyl Acetate). The blends or formulations described herein were selected through standardized performance tests on solvency of alkyd paints and evaporation rate tests in comparison to mineral spirits.

The odor of the blends was also tested empirically. Evaporation rates were calculated based on weight averages (% by volume) of individual components based on relative evaporation rate vs. n-butyl acetate.

TABLE 1

|  | Propylene Carbonate | Decamethyl tetrasiloxane | p-Chlorobenzo trifluoride | Mineral Spirits | Calculated Evaporation rate | Predicted Flash Point[1] |
|---|---|---|---|---|---|---|
| Formulation 1 | 5 | 35 | 60 | 0 | 0.59 | 52.6° C. |
| Formulation 2 | 5 | 35 | 65 | 0 | 0.63 | 51.9° C. |
| Formulation 3 | 7.5 | 30 | 62.5 | 0 | 0.61 | 54.2° C. |
| Formulation 4 | 10 | 30 | 60 | 0 | 0.59 | 56.5° C. |
| Formulation 5 | 10 | 25 | 65 | 0 | 0.62 | 55.8° C. |
| Formulation 6 | 10 | 35 | 55 | 0 | 0.55 | 57.2° C. |
| Formulation 7 | 10 | 27 | 63 | 0 | 0.61 | 56.0° C. |
| Formulation 8 | 11 | 29 | 60 | 0 | 0.58 | 57.2° C. |
| Formulation 9 | 12 | 28 | 60 | 0 | 0.58 | 58.0° C. |
| Formulation 10 | 13 | 27 | 60 | 0 | 0.58 | 58.8° C. |
| Formulation 11 | 14 | 26 | 60 | 0 | 0.58 | 59.6° C. |
| Formulatton 12 | 15 | 25 | 60 | 0 | 0.58 | 60.4° C. |
| Formulation 13 | 20 | 20 | 60 | 0 | 0.57 | 64.2° C. |
| Formulation 14 | 25 | 15 | 60 | 0 | 0.56 | 68.1° C. |
| Formulation 15 | 10 | 38 | 52 | 0 | 0.53 | 57.6° C. |
| Formulation 16 | 10 | 39 | 51 | 0 | 0.52 | 57.7° C. |
| Formulation 17 | 10 | 40 | 50 | 0 | 0.51 | 57.9° C. |
| Formulation 18 | 10 | 41 | 49 | 0 | 0.50 | 58.0° C. |
| Formulation 19 | 10 | 42 | 48 | 0 | 0.50 | 58.1° C. |
| Formulation 20 | 0 | 50 | 50 | 0 | 0.53 | 50.1° C. |
| Formulation 21 | 12 | 23 | 65 | 0 | 0.62 | 57.3 |
| Formulation 22 | 0 | 0 | 0 | 100 | 0.1 | 42° C. |

Formulations that contained less than 50% (v/v) PCBTF (Formulations 18, 19) were observed to be immiscible as a solvent blend.

Formulations that contained more than 12% (v/v) PC (Formulations 10-14) were observed to be immiscible with alkyd paint/mineral spirits.

TABLE 2

| Blend | Formulation 22 | Formulation 4 | Formulation 5 | Formulation 6 | Formulation 7 |
|---|---|---|---|---|---|
| Time required (seconds) | 395 | 457 | 297 | 473 | 372 |

Formulations 4-7 were subjected to comparative evaporation rate tests versus mineral spirits (Formulation 22) (Table 2; average of 3 trials). Uniform pieces of paper were individually wet with each solvent and the amount of time required for the paper to dry was qualitatively observed. Formulation 7 was found to have the closest drying time to mineral spirits (Formulation 22).

In the preceding description, for purposes of explanation, numerous details are set forth in order to provide a thorough understanding of the examples. However, it will be apparent to one skilled in the art that these specific details are not required.

The above-described examples are intended to be exemplary only. Alterations, modifications and variations can be effected to the particular examples by those of skill in the art without departing from the scope, which is defined by the claims appended hereto.

What is claimed is:

1. A solvent composition comprising:
   i) para-Chlorobenzotrifluoride (PCBTF) comprising about 60% to about 65% by volume of the solvent composition;
   ii) a methylated organosilicon compound comprising about 23% to about 50% by volume of the solvent composition; and
   iii) a carbonate ester comprising about 0% to about 12% by volume of the solvent composition.

2. The solvent composition of claim 1 wherein:
   i) the methylated organosilicon compound comprises about 25% to about 30% by volume of the solvent composition; and
   ii) the carbonate ester comprises about 10% to about 12% by volume of the solvent composition.

3. The solvent composition of claim 1 wherein the methylated organosilicon compound or the carbonate ester is VOC-exempt.

4. The solvent composition of claim 1 wherein the carbonate ester is propylene carbonate (PC).

5. The solvent composition of claim 1 wherein the methylated organosilicon compound is hexamethyldisiloxane (HMDS), octamethyltrisiloxane (OMTS), or decamethyltetrasiloxane (DMTS).

6. The solvent composition of claim 1 wherein:
   i) the para-Chlorobenzotrifluoride (PCBTF) comprises about 60% by volume of the solvent composition;
   ii) the methylated organosilicon compound is decamethyltetrasiloxane (DMTS), and comprises about 28% by volume of the solvent composition; and
   iii) the carbonate ester is propylene carbonate (PC) and comprises about 12% by volume of the solvent composition.

7. The solvent composition of claim 1 wherein:
   i) the para-Chlorobenzotrifluoride (PCBTF) comprises about 63% by volume of the solvent composition;
   ii) the methylated organosilicon compound is decamethyltetrasiloxane (DMTS), and comprises about 27% by volume of the solvent composition; and
   iii) the carbonate ester is propylene carbonate (PC) and comprises about 10% by volume of the solvent composition.

8. The solvent composition of claim 1 wherein:
   i) the para-Chlorobenzotrifluoride (PCBTF) comprises about 65% by volume of the solvent composition;
   ii) the methylated organosilicon compound is decamethyltetrasiloxane (DMTS), and comprises about 25% by volume of the solvent composition; and
   iii) the carbonate ester is propylene carbonate (PC) and comprises about 10% by volume of the solvent composition.

9. The solvent composition of claim 1 wherein the solvent composition has a calculated flash point of at least 50° C.

10. The solvent composition of claim 1 wherein the solvent composition has a calculated evaporation rate of at most 0.7.

11. A kit or commercial package comprising the solvent composition of claim 1 together with instructions for use.

12. The solvent composition of claim 1 wherein the solvent composition is for use as a replacement for slow evaporating solvents.

13. The solvent composition of claim 1 for use as a replacement for mineral spirits, methyl amyl ketone (mak), cyclohexane, n-butyl acetate, Aromatic 100 or Aromatic 150.

14. The solvent composition of claim 1 for use as a solvent.

15. The solvent composition of claim 1 for use as a primary or co-solvent for paints, varnishes, coatings, inks, or adhesives.

16. The solvent composition of claim 1 for use in the manufacturing and/or formulation of paints, varnishes, coatings, wood preservatives, lacquers, or varnishes.

17. The solvent composition of claim 1 for use as a paint thinner, paint remover, cleaner, degreaser, and/or adhesive remover.

18. The solvent composition of claim 2, wherein the carbonate ester is propylene carbonate (PC).

19. The solvent composition of claim 2, wherein the methylated organosilicon compound is hexamethyldisiloxane (HMDS), octamethyltrisiloxane (OMTS), or decamethyltetrasiloxane (DMTS).

* * * * *